United States Patent [19]

Procter et al.

[11] Patent Number: 4,594,249

[45] Date of Patent: Jun. 10, 1986

[54] METHOD OF ALTERING INTOXICATING EFFECTS OF ALCOHOL

[75] Inventors: Richard W. Procter, Minneapolis; Stanton L. Anondson, St. Louis Park, both of Minn.

[73] Assignee: 21st Century Marketing, Inc., St. Louis Park, Minn.

[21] Appl. No.: 745,019

[22] Filed: Jun. 14, 1985

[51] Int. Cl.$^4$ ............................................. A61K 33/44
[52] U.S. Cl. ..................................................... 424/125
[58] Field of Search ........................................ 424/125

[56] References Cited

U.S. PATENT DOCUMENTS 3,934,007 1/1976 Gussin et al. ...................... 424/125
4,122,169 10/1978 Geils ................................... 424/125

Primary Examiner—Stanley J. Friedman
Attorney, Agent, or Firm—Burd, Bartz & Gutenkauf

[57] ABSTRACT

A method of altering the intoxicating effects of beverage alcohol by the ingestion of activated charcoal prior to, along with, and/or immediately following the consumption of alcohol. Absorption of alcohol and its metabolites from the digestive tract into the circulatory system is reduced. This has the effect of reducing the symptoms associated with alcohol intoxication. Reverse absorption of alcohol and its metabolites from the cirulatory system to the digestive tract by ingestion of activated charcoal during or following the consumption of alcohol reduces or eliminates the hang-over effect. Long term alcohol-related disabilities may be reduced or eliminated.

8 Claims, No Drawings

METHOD OF ALTERING INTOXICATING EFFECTS OF ALCOHOL

FIELD OF THE INVENTION

Background of the Invention

This invention is directed to a method of altering the intoxicating effects of beverage alcohol. In the immediate short term, it reduces the effects of intoxication from the consumption of more than moderate quantities of alcohol by reducing symptoms such as slurred speech, unsteadiness, lack of coordination, etc. and by reducing blood alcohol levels. In the longer short term, it reduces or eliminates the next day effects of alcohol consumption known as hang-over. In the long run, the method eliminates or reduces the long term effects of heavy consumption of alcohol: depression, delirium tremens, peptic ulcers, cirrhosis of the liver, fetus damage, pancreatitis, alcohol-related death, and associated alcohol-related disabilities. The method is based on the consumption by the subject of activated charcoal before, during and/or following consumption of alcohol.

The Prior Art

Activated charcoal has high adsorptive capacity. As a result, it has been used as a folk remedy for intestinal problems in humans for many years. Activated charcoal has also been used as an antidote in the treatment of various kinds of poisoning, such as methanol or wood alcohol poisoning. With one exception, the effect of activated charcoal on reducing the aftereffects of alcohol consumption has gone unnoticed. Over twenty years ago, the ingestion of capsules of activated charcoal was briefly promoted as a morning after remedy taken as a hang-over cure. This venture was short-lived, perhaps because until as late as 1975 activated charcoal was not available as a recognized drug in the United States and commercial preparations of charcoal usually contained warnings against use in human subjects.

North et al (Am. J. Hosp. Pharm., 1981: 38: 864–6) studied the effect of activated charcoal on ethanol blood levels following oral administration of ethanol in dogs. It was found that a single massive dose of activated charcoal in a water slurry administered before ingestion of ethanol significantly lowered blood ethanol levels measured at one-half, one, two and three hours after administration of the ethanol.

Neuvonen et al (Acta. pharmacol. et toxicol., 1984, 54, 1–7) studied the effect of ethanol on the adsorption of aspirin and quinidine sulfate on activated charcoal in six healthy human volunteers. It was found that the bioavailability of both aspirin and quinidine was significantly reduced by the activated charcoal. It was also found that the concomitant ingestion of alcohol with the drugs antagonized only slightly the ability of the charcoal to reduce the absorption of aspirin and quinidine by the system of the subject. However, it was concluded that the absorption of ethanol into the circulatory system was not significantly prevented by activated charcoal.

In every instance in the prior art studies, the activated charcoal was administered as a single dose, in most instances a massive dose.

SUMMARY OF THE INVENTION

Broadly stated, the present invention is directed to a method for alleviating the effects of consumption of beverage alcohol which comprises administering to the drinker of alcohol an amount of activated charcoal equal to at least about 5 to 15 milligrams of charcoal per kilogram of body weight. Preferably the charcoal is administered in from two to four minimum doses spread over the period of alcohol consumption, depending upon its length and the amount of alcohol consumed.

DETAILED DESCRIPTION OF THE PREFERRED EMBODIMENT

Activated charcoal is a fine, black, insoluble powder, without taste or odor. After preparation by combustion of organic material such as wood or vegetables, it is activated by an oxidizing gas flow at high temperature. This process produces a fine network of pores in the internal surfaces. The internal surface area formed by pores is much larger than the external surface area. For example, the total surface area of activated charcoal is on the order of 1,000 meters per gram, while the total pore volume is about 1 cubic centimeter per gram. The pore sizes range from about 10 angstroms to more than 100,000 angstroms. Activated charcoal is commercially available in many different grades and under a variety of brand names, such as Carboraffin, Medicoal, Norit, Opocarbyl, Ultracarbon, etc.

Although activated charcoal may be administered to a subject in a variety of forms, it is preferably given in the form of loose powder packaged in capsules of gelatin or other water-soluble encapsulating material. Capsules may contain convenient dosage quantities in the range from about 100 to 500 milligrams per capsule. Activated charcoal may also be administered in tablet form preferably in dose sizes of from about 50 to 300 milligrams per tablet.

Large doses of activated charcoal, such as might be given as an antidote to poison in amounts of 50 grams or more, are usually administered in water suspension. However, charcoal suspension adheres to the mucosal surfaces of the throat, giving a chalk-like taste which is objectionable to some. Such large doses are not administered in the practice of the present invention. Administration by capsule or tablet is preferred. Capsules and tablets have the additional advantage that they are easy to carry in anticipation of a convivial event at which alcohol is served. They are also easily packaged for sale by bars, cocktail lounges, taverns, and the like, either over the counter or through vending machines, for use at the time of alcohol consumption.

For alleviation of the results of drinking, the activated charcoal is preferably self-administered concomitantly with the drinking. Ideally the first dose is taken shortly before or at the time of beginning to drink. This initial dose should preferably be between about 5 and 15 milligrams of activated charcoal per kilogram of body weight. For example, a 160 pound man, whose weight in kilograms is 72.6, taking two 350 milligram capsules, is receiving approximately 10 milligrams per kilogram of body weight.

The dosage is preferably repeated at intervals of one to three hours as the course of alcohol consumption continues, dependent upon the amount of alcohol consumed. A light to moderate drinker consuming one to two beverages per hour, whether in the form of beer, wine, cocktails, highballs, or the like, should repeat the dosage every two to three hours. On the other hand, a heavy drinker consuming three to four beverages per hour should preferably repeat the dosage every one to two hours. A further dose of activated charcoal of the same size should be taken at the end of the drinking session in order to avoid the hang-over aftereffects of alcohol consumption, which afflict some persons.

It is well known that alcohol ingested into the digestive tract is quickly absorbed into the circulatory system. The use of activated charcoal over a period of time, along with the consumption of alcohol, reduces but does not eliminate the absorption of alcohol into the blood stream. It is commonly thought that ethanol and whatever else is associated with it in the drink are metabolized into various products. Some of these metabolites of ethanol are absorbed by the blood stream and are believed to cause some of the euphoria seen during alcohol intoxication, as well as some of the deleterious effects of intoxication. These metabolites are adsorbed by activated charcoal along with ethanol.

Once the metabolites of ethanol are produced and are in circulation in the blood stream, they can have long lasting effects on many different systems in the body. Recently two articles in the New England Journal of Medicine (Sept. 9, 1982, Volume 307, No. 11) have shown that activated charcoal has an effect on both the absorption and elimination of several drugs. Berg et al (pages 642–644) have shown that, although phenobarbitol was completely absorbed into the circulatory system from the gut, when activated charcoal is administered there is an excretion of phenobarbitol and/or its metabolites back into the gut. Since the activated charcoal causes the phenobarbitol which is in the circulatory system to be pulled from the circulation into the gut, this process sets up diffusion gradients in favor of promoting the excretion of the phenobarbitol back into the gut with its consequent removal in the feces. Levy (pages 676–678) reports similar results on absorption and elimination of phenobarbitone, carbanazepine and phenyl-butazone. In both instances, large doses of from 50 to 100 grams of activated charcoal were administered.

The administration of activated charcoal at the end of the beverage alcohol drinking has a similar effect in clearing ethanol and its metabolites from the circulatory system back into the intestinal tract. Once the activated charcoal begins to adsorb some of the ethanol and its metabolites after they have left the intestinal tract, a concentration gradient is created in favor of movement of the compounds back into the gut. As a consequence, the number of compounds that are circulating in the body after the complete ingestion of ethanol is minimized, along with the physiological effects of those compounds.

The preferred practice of administering multiple doses of activated charcoal over a period of time, prior to or at the beginning of drinking, in the midst of an extended drinking period and upon completion of drinking, has real value. Adsorption of alcohol on the activated charcoal minimizes the amount of ethanol leaving the digestive tract. Ingestion of activated charcoal at the end of the drinking period brings back into the intestinal tract at least some of the ethanol and its metabolites. The substantial reduction or elimination of those substances which lead to the long term deleterious effects of consumption of alcohol substantially reduces or eliminates those long term effects. Some conditions such as cirrhosis of the liver, are probably irreversible. However, progression of the disease can be substantially slowed or halted as a result of reduction or elimination of the contributing causes through administration of activated charcoal. Other long term conditions, such as depression, peptic ulcers, and the like, are reversible and can be cured once their progression has been halted by removal of the contributing causes.

The invention is further illustrated by the following examples:

EXAMPLE 1

A white male subject weighing approximately 170 pounds (77 kilograms) took two 350 milligram capsules of activated charcoal. Then, over the course of 1 hour, 6 ounces of ethanol were consumed. Twelve minutes following consumption of the last drink, the blood alcohol level was tested at 0.08 percent, using a portable, calibrated breathalyzer. After an additional five minutes, the blood alcohol level was reduced to 0.05 percent. After an additional thirteen minutes, thirty minutes after completion of the last drink, the blood alcohol level was reduced to 0.04 percent. Based upon the standard charts relating blood alcohol levels to the amount of alcohol consumption and body weight, the blood alcohol concentration should have been over 0.10 percent, the standard for measuring drunkenness in most states.

EXAMPLE 2

In a parallel experiment conducted at the same time, another white male subject weighing about 170 pounds (77 kilograms) also took two 350 milligram capsules of activated charcoal immediately before drinking six ounces of alcohol over the course of one hour. His blood alcohol level was measured at 0.13 percent eight minutes following completion of the last drink. Six minutes later, it measured 0.06 percent and sixteen minutes later, thirty minutes after completion of the last drink, it measured 0.04 percent. Again, according to the standard charts, the blood alcohol level should have been over 0.10 percent.

EXAMPLE 3

The subject of Example 1 participated in another experiment. Two 350 milligram capsules of activated charcoal were ingested at the beginning of the test. Twenty-one ounces of alcohol were consumed over a period of four hours. Two more 350 milligram capsules of activated charcoal were ingested five minutes before the end of the test. Eighteen minutes following completion of the last drink, the subject's blood alcohol was measured at 0.145 percent. Thirty minutes later, it was tested at 0.11 percent. Forty minutes later, it was tested at 0.09 percent, and fifty-five minutes later it was also tested at 0.09 percent. According to the standard charts, the blood alcohol level should have been at least 0.2 percent had the activated charcoal not been taken. This experiment was conducted in the evening but no morning after effect was experienced. When similar amounts of alcohol were consumed by this subject without activated charcoal, classic hang-over symptoms were observed.

EXAMPLE 4

The subject of Example 2 participated in another experiment as follows: At the beginning of the test, two 350 milligram capsules of activated charcoal were ingested. Six ounces of alcohol were consumed in a period of one hour. Thirty minutes later, two more 350 milligram capsules of activated charcoal were ingested and immediately thereafter the blood alcohol level was tested at 0.04 percent. Nine more ounces of alcohol were consumed over the next two and one-half hours. Sixteen minutes following completion of the last drink, the blood alcohol level was measured at 0.125 percent. Eleven minutes later, it was measured at 0.055 percent. Nineteen minutes later, it was measured at 0.05 percent. According to the standard charts, the blood alcohol level for this subject should likewise have been at least 0.20 percent. This experiment was also conducted in the evening and again no hang-over effect was noted, although this subject ordinarily suffers from hang-over after consumption of similar amounts of alcohol.

It is apparent that many modifications and variations of this invention as hereinbefore set forth may be made without departing from the spirit and scope thereof. The specific embodiments described are given by way of example only and the invention is limited only by the terms of the appended claims.

We claim:

1. A method for alleviating the effects of consumption of beverage alcohol which comprises administering to the drinker of alcohol at least one dose of activated charcoal in an amount equal to at least about 5 to 15 milligrams of charcoal per kilogram of body weight, said charcoal being administered substantially concurrently with the consumption of alcohol.

2. A method according to claim 1 wherein said activated charcoal is administered immediately before or at the beginning of a period of consumption of alcohol.

3. A method according to claim 1 wherein said activated charcoal is administered in the midst of a period of alcohol consumption.

4. A method according to claim 1 wherein said activated charcoal is administered at the end of or following shortly after a period of consumption of alcohol.

5. A method according to claim 1 wherein said activated charcoal is administered in from two to four time-spaced doses, each of at least about 5 to 15 milligrams of charcoal per kilogram of body weight, over the period of alcohol consumption.

6. A method according to claim 5 wherein a first dose of activated charcoal is administered immediately before or at the beginning of a period of consumption of alcohol and another dose of activated charcoal is administered at the end of or shortly following the period of alcohol consumption.

7. A method according to claim 5 wherein a first dose of activated charcoal is administered immediately before or at the beginning of a period of alcohol consumption, at least one further dose of activated charcoal is administered during the period of alcohol consumption, and a further dose of activated charcoal is administered at the end of or shortly following the period of alcohol consumption.

8. A method according to claim 5 wherein a first dose of activated charcoal is administered in the midst of a period of consumption of alcohol and another dose of activated charcoal is administered at the end of or shortly following the period of alcohol consumption.

* * * * *